US012259521B2

(12) United States Patent
Koo et al.

(10) Patent No.: US 12,259,521 B2
(45) Date of Patent: Mar. 25, 2025

(54) METHOD AND SYSTEM OF ANALYZING INGREDIENTS OF ARTIFICIAL RAINFALL FOR VERIFICATION OF CLOUD SEEDING EFFECT

(71) Applicant: National Institute of Meteorological Sciences, Seogwipo-si (KR)

(72) Inventors: Hae Jung Koo, Seogwipo-si (KR); Ki Ho Chang, Seoul (KR); Joo Wan Cha, Seogwipo-si (KR); Hyunjun Hwang, Pyeongchang-gun (KR); Minhoo Kim, Pyeongchang-gun (KR); Woon Seon Jung, Seogwipo-si (KR); Jung Mo Ku, Seogwipo-si (KR); Ji Man Park, Seogwipo-si (KR); Miloslav Belorid, Seogwipo-si (KR); Sang Hee Chae, Seogwipo-si (KR); Ha-Young Yang, Siheung-si (KR); Chulkyu Lee, Seoul (KR); Ji Min Woo, Incheon (KR); Eun Hye Sim, Seoul (KR); Chang Hee Kang, Jeju-si (KR); Jung Min Song, Jeju-si (KR)

(73) Assignee: National Institute of Meteorological Sciences, Seogwipo-si (KR)

( * ) Notice: Subject to any disclaimer, the term of this patent is extended or adjusted under 35 U.S.C. 154(b) by 0 days.

(21) Appl. No.: 17/682,828

(22) Filed: Feb. 28, 2022

(65) Prior Publication Data
US 2022/0357482 A1 Nov. 10, 2022

(30) Foreign Application Priority Data
May 4, 2021 (KR) .................. 10-2021-0058024

(51) Int. Cl.
*G01W 1/14* (2006.01)
*A01G 15/00* (2006.01)
(Continued)

(52) U.S. Cl.
CPC .............. *G01W 1/14* (2013.01); *G01N 33/18* (2013.01); *G01N 33/1813* (2013.01);
(Continued)

(58) Field of Classification Search
CPC ........... G01W 1/14; G01W 1/06; G01W 1/08; G01W 1/10; G01W 2201/00;
(Continued)

(56) References Cited

U.S. PATENT DOCUMENTS

2018/0082001 A1* 3/2018 Yang ..................... A01G 15/00
2018/0246014 A1* 8/2018 Lee .......................... G01W 1/14

FOREIGN PATENT DOCUMENTS

WO WO-2020121301 A1 * 6/2020

OTHER PUBLICATIONS

Fisher, James M., et al. "Assessment of ground-based and aerial cloud seeding using trace chemistry." Advances in Meteorology 2018 (2018). (Year: 2018).*

(Continued)

*Primary Examiner* — Yoshihisa Ishizuka
*Assistant Examiner* — Carter W Ferrell
(74) *Attorney, Agent, or Firm* — You & IP, LLC

(57) ABSTRACT

Provided are a method and system of analyzing ingredients of an artificial rainfall for verification of a cloud seeding effect. As the method and system, which can verify an effect of the artificial rainfall in such a manner that a seeding material becomes different according to each temperature of clouds at a seeding altitude, water sampling from precipitation is performed before and after seeding, and thus the ingredients of a water sample are analyzed using each of a method of analyzing a heavy metal component and a method of analyzing a water-soluble ion component according to a cool cloud and a warm cloud so that whether or not there is a change in each concentration of the ingredients can be (Continued)

determined, are provided, an experiment for the artificial rainfall can more effectively be performed.

6 Claims, 8 Drawing Sheets

(51) Int. Cl.
G01N 33/18 (2006.01)
G01W 1/06 (2006.01)
G01W 1/10 (2006.01)

(52) U.S. Cl.
CPC .............. G01W 1/06 (2013.01); A01G 15/00 (2013.01); G01W 1/10 (2013.01)

(58) Field of Classification Search
CPC .... G01N 33/1813; G01N 33/18; A01G 15/00; Y02A 90/10
See application file for complete search history.

(56) References Cited

OTHER PUBLICATIONS

Silverman, Bernard A., and Wathana Sukarnjanaset. "Results of the Thailand warm-cloud hygroscopic particle seeding experiment." Journal of Applied Meteorology and Climatology 39.7 (2000): 1160-1175. (Year: 2000).*

Warburton, Joseph A., et al. "The assessment of snowpack enhancement by silver iodide cloud-seeding using the physics and chemistry of the snowfall." The Journal of Weather Modification 28.1 (1996): 19-28. (Year: 1996).*

Fisher, James M., Marion L. Lytle, and Shawn G. Benner. "Evaluation of glaciogenic cloud seeding using trace chemistry." The Journal of Weather Modification (2016). (Year: 2016).*

Craig, I., et al. "The SE Queensland Cloud Seeding Research Program." Society for Engineering in Agriculture (Australia). Brisbane, Queensland: Engineers Australia, 2009. 521. (Year: 2009).*

Rosenfeld, Daniel, et al. "Targeting and impacts of Agl cloud seeding based on rain chemical composition and cloud top phase characterization." Atmospheric Research (2003): 114-115. (Year: 2003).*

* cited by examiner

METHOD AND SYSTEM OF ANALYZING INGREDIENTS OF ARTIFICIAL RAINFALL FOR VERIFICATION OF CLOUD SEEDING EFFECT

BACKGROUND OF THE INVENTION

Field of the Invention

The present invention relates to a method and system of analyzing ingredients of an artificial rainfall for verification of a cloud seeding effect, and more particularly, to a direct verification method using the selection of a main region in which an effect occurs (i.e., a downwind region which is affected by a diffusion reaction of a seeding material), and a region in which no effect occurs (i.e., an upwind region in which no seeding material is diffused), and the analysis of main ingredients (i.e., ion and heavy metal components) of precipitation before and after seeding according to an experiment for an artificial rainfall (i.e., cloud seeding).

Description of the Related Arts

In Korea and other countries, technologies for adjusting weather conditions using experiments for an artificial rainfall have been tried for the purpose of studying a decrease in disasters, such as a possibility of causing a decrease in fogs, and a decrease in minute dust, as well as the purpose of bringing about a decrease in drought by securing water resources, and preventing forest fires. In particular, according to the introduction of a weather aircraft in 2018, and the establishment of a basic plan for an artificial rainfall in 2020 to 2024, the number of times that an experiment for an artificial rainfall can be performed for the year increased or will increase (expected to be 50 times or more in 2024), and thus studies of verifying an effect and effectiveness resulting from the experiment have also been promoted.

Main methods of verifying an experimental effect of an artificial rainfall are performed using the identification of a change in precipitation amount of the ground, cloud physics-based observations using a meteorological aircraft, observations on a change in size of precipitation cloud particles according to each time, the analysis of a change in accumulated precipitation amount shown in each of a region which is affected by seeding according to a numerical simulation, and a region which is affected by non-seeding, the identification of a change in radar reflectance, and so on. Even though these methods can be identified by comparative observations before and after seeding, there is a limit which shows that it is difficult to directly verify a main ingredient (i.e., icing nucleus matter or hygroscopic matter) of artificial rainfall matter included in precipitation or a cloud. Accordingly, it has been required, for a direct verification way for verification of an effect resulting from an experiment for an artificial rainfall, to develop an analysis technique for main chemical ingredients (i.e., an ion and heavy metal) using each definition of concepts concerning a main region in which an effect occurs, and a region in which no effect occurs, and the observations of precipitation.

SUMMARY OF THE INVENTION

According to technical solutions of the present invention, which has been made for solving the aforesaid problems, the present invention provides each definition of the concepts of a region (a target region) in which a main effect occurs, and a region in which no effect occurs (the region in which no effect occurs is selected from an upwind area in which no seeding material is diffused) according to an experiment for an artificial rainfall (i.e., cloud seeding) targeted for a cool cloud having a temperature of 0° C. or below and a warm cloud having a temperature of 0° C. or more, and also provides a method of analyzing chemical ingredients of precipitation, and a direct verification technology.

Furthermore, it is provided to distinguish a method of analyzing chemical ingredients of precipitation based on a cool cloud from a method of analyzing chemical ingredients of a rainfall based on a warm cloud, and to verify an effect resulting from an experiment for an artificial rainfall using an analysis method suitable for each of the clouds.

The technical solutions of the present invention are not limited to those as mentioned above, and other solutions which are not mentioned can clearly be understood by those having ordinary skill in the art based on the following description.

In order to solve the aforesaid technical problems, according to one embodiment of the present invention, a method of analyzing ingredients of an artificial rainfall for verification of a cloud seeding effect, comprises: (A) calculating a scope in which a seeding material is diffused, and which is affected by the seeding material when a seeding condition for the artificial rainfall is decided by weather information collected; (B) selecting a first region, namely, a main region which is largely affected by diffusion of the seeding material, and a second region which is slightly affected by diffusion of the seeding material in consideration of the scope which is affected by the seeding material; (C) performing water sampling from precipitation according to each time zone before and after seeding in the first region and the second region; (D) analyzing ingredients of matter included in the a water sample according to each temperature of clouds at a seeding altitude; and verifying an effect of the artificial rainfall by determining a change of a reference ingredient extracted in each of the first region and the second region.

In case that a cloud has a temperature of 0° C. or below at the seeding altitude, said step (D) shows analyzing a heavy metal component with respect to ingredients of icing nucleus matter included in a water sample, thereby analyzing whether or not a reference ingredient is detected before and after seeding, and a change in mass, wherein the reference ingredient is the heavy metal component.

In case that the icing nucleus mater is silver iodide, the reference ingredient is silver.

In case that a cloud has a temperature of 0° C. or more at the seeding altitude, said step (D) shows analyzing a water-soluble ion component with respect to ingredients of condensation nucleus matter included in a water sample, and thus analyzing whether or not a reference ingredient is detected before and after seeding, and a change in mass, wherein the reference ingredient is the water-soluble ion component.

In case that the condensation nucleus matter is calcium chloride, the reference ingredient is a calcium ion.

Said step (E) shows determining that an effect resulting from an experiment for the artificial rainfall occurs in the first region when it is determined that there is a meaningful change in concentration of the reference ingredient before and after seeding.

Meanwhile, according to another embodiment of the present invention, a system of analyzing ingredients of an artificial rainfall for verification of a cloud seeding effect comprises: a seeding scope calculation unit configured to calculate a scope in which a seeding material is diffused, and which is affected by the seeding material when a seeding condition for the artificial rainfall is decided by weather information collected; a region selection unit configured to select a first region, namely, a main region which is largely affected by diffusion of the seeding material, and a second region which is slightly affected by diffusion of the seeding material in consideration of the scope which is affected by the seeding material; a precipitation-based water sampling unit configured to perform water sampling from precipitation according to each time zone before and after seeding in the first region and the second region; a water sampling analysis unit configured to analyze ingredients of matter included in a water sample according to each temperature of clouds at a seeding altitude; and an effect verification unit configured to verify an effect of the artificial rainfall by determining a change of a reference ingredient extracted in each of the first region and the second region.

In case that a cloud has a temperature of 0° C. or below at the seeding altitude, the water sampling analysis unit analyzes a heavy metal component with respect to ingredients of icing nucleus matter included in a water sample, thereby analyzing whether or not a reference ingredient is detected before and after seeding, and a change in mass, wherein the reference ingredient is the heavy metal component.

In case that the icing nucleus matter is silver iodide, the reference ingredient is silver.

In case that a cloud has a temperature of 0° C. or more at the seeding altitude, the water sampling analysis unit analyzes a water-soluble ion component with respect to ingredients of condensation nucleus matter included in a water sample, thereby analyzing whether or not a reference ingredient is detected before and after seeding, and a change in mass, wherein the reference ingredient is the water-soluble ion component.

In case that the condensation nucleus matter is calcium chloride, the reference ingredient is a calcium ion.

The effect verification unit determines that an effect resulting from an experiment for the artificial rainfall occurs in the first region when it is determined that there is a meaningful change in concentration of the reference ingredient before and after seeding.

According to the present invention, each definition of the concepts of a main region (i.e., a target region) in which an effect occurs, and a region in which no effect occurs (i.e., selecting the region in which no effect occurs from an upwind area in which no seeding material is diffused) according to an experiment for an artificial rainfall (cloud seeding) targeted for a cool cloud (having a temperature of 0° C. or below) and a warm cloud (having a temperature of 0° C. or more), can be provided, and a method of analyzing chemical ingredients of the rainfall, and a direct verification technology can also be provided.

Furthermore, the methods of analyzing chemical ingredients of precipitation based on the cool cloud and the warm cloud are distinguished from each other, and an effect resulting from the experiment for the artificial rainfall can be verified using the analysis method suitable for each cloud.

Also, each definition of concepts of the main region in which the effect occurs, and the region in which no effect occurs according to this experiment for an artificial snowfall (or rainfall), and a technology for analyzing ingredients of precipitation are effective in that they can be used as direct verification means concerning the analysis of an effect resulting from the experiment for the artificial rainfall as well as the identification of a change in concentration properties shown in time and space of the ingredients of matter included in precipitation before and after the experiment. Thus, they can contribute to the activity of a technology for an artificial rainfall.

The effects of the present invention are not limited to those as mentioned above, and other effects which are not mentioned can clearly be understood by those having ordinary skill in the art based on the following description.

DETAILED DESCRIPTION OF THE INVENTION

Figure 1:
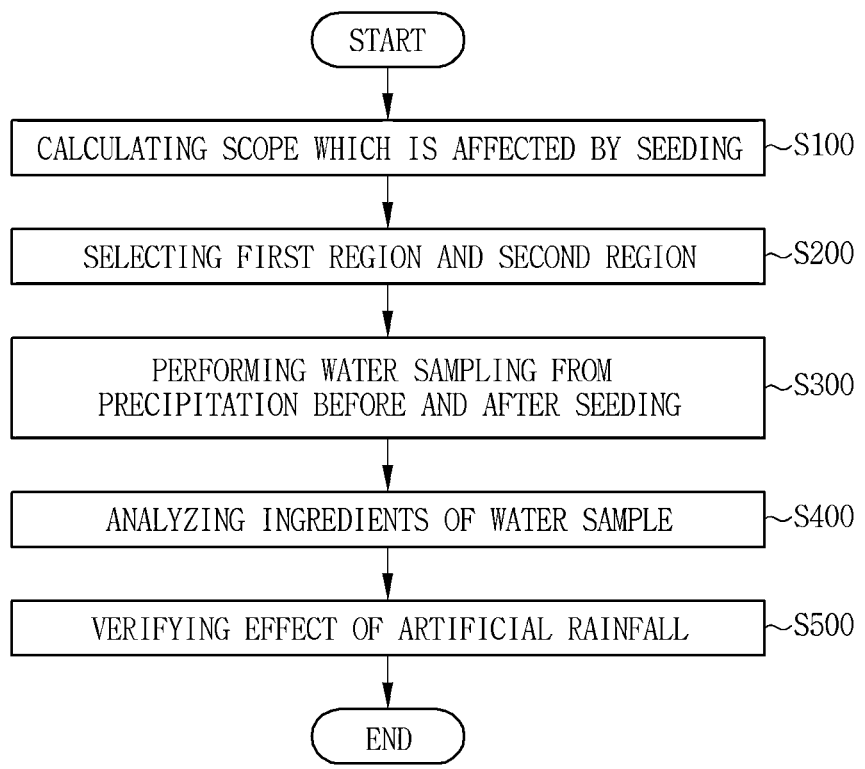
FIG. 1 is a flow chart showing a method of analyzing ingredients of an artificial rainfall according to one embodiment of the present invention.

The objects, other objects, features, and advantages of the present invention as mentioned above could easily be understood based on the accompanying drawings and the following preferable embodiments related therewith. However, the present invention should not be construed as limited to the embodiments set forth herein, but may be embodied in different forms. Rather, these embodiments introduced herein are provided so that the contents disclosed herein can be thorough and complete, and can fully convey the scope of the present invention to those skilled in the art.

In case that the terms, such as a first term, a second term, and so on used in the present specification are intended for describing the elements, these elements should not be limited by these terms. These terms are only used for causing one constituent element to be distinguished from another constituent element. The embodiments described and exemplified herein may include supplementary embodiments thereof.

Furthermore, in case that it is mentioned that an element, constituent element, device, or system comprises a constituent element composed of a program or software, although it is not clearly described, the element, constituent element, device, or system should be understood as including hardware (ex., a memory, a CPU, and so on) or different programs, or software (ex., a driver and so on intended for driving an operational system or hardware) which is necessary for putting the program or software into practice or operation.

The terms used in the present specification are intended for describing the embodiments and are not intended to be limiting of the present invention. In the present specification, the singular forms "a," "an" and "the" are intended to include the plural forms as well, unless the context clearly indicates otherwise. The terms "comprises" and/or "comprising" used herein should not be construed as excluding the existence or addition of one or more other constituent elements due to any mentioned constituent element.

In the description of the following specific embodiments, various specific contents are prepared to provide a further specific description and understanding of the present invention. However, a reader, who has knowledge in the relevant field in such a degree that he or she can understand the present invention, may recognize that although there are not these various specific contents, the embodiments can be used.

It is previously mentioned that in any case, parts, which have been well-known in the relevant field of the present invention, but are not largely related to the present invention, are omitted in the description of the present invention in order to avoid causing confusion without a special reason.

In order to accomplish the objects, a method and system of analyzing ingredients of an artificial rainfall according to embodiments of the present invention are intended for carrying out verification concerning a main region which is affected by a seeding material, and a region which is not affected by a seeding material by analyzing main ingredients (ion and heavy metal components) of precipitation according to an experiment for an artificial rainfall (i.e., cloud seeding).

The seeding material of the artificial rainfall is largely decided as two kinds of matter according to each temperature of clouds at a height of seeding being carried out.

When a cloud has a temperature of 0° C. or below existing at a seeding altitude (i.e., a cool cloud), icing nucleus matter (including silver iodide and dry ice as main ingredients), which causes the cloud to grow into snowfall (or precipitation) particles through an icing Meanwhile, when a cloud has a temperature of 0° C. or more at a seeding altitude (i.e., a warm cloud), hygroscopic condensation nucleus matter (including calcium chloride and sodium chloride as main ingredients), which causes droplet particles to grow and to thereby fall as a rainfall as a big condensation nucleus induces or strengthens a process of generating large droplets, and a collision and combination process among droplets, is mainly used.

The present invention relates to a method that is devised to overcome the limit of an indirect verification method concerning a seeding effect based on a change in cloud physics-based data observed from an aircraft and the ground, a change in radar reflectance, a numerical simulation, and so on, and to directly analyze main chemical ingredients of precipitation of the main region in which the effect occurs, and the region in which no effect occurs according to the seeding experiment so that the effect can be verified.

Hereinafter, the detailed technical contents to be embodied in the present invention will be described in detail with reference to the accompanying drawings.

Figure 2:
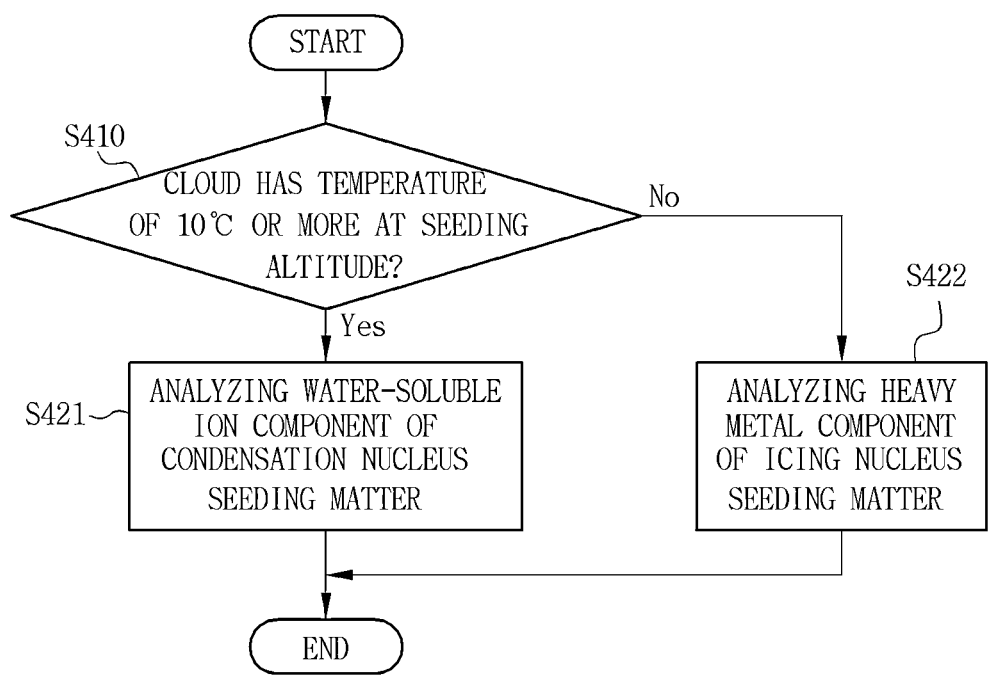
FIG. 2 is a detailed flow chart showing analyzing ingredients of water sampling matter shown in FIG. 1.
Figure 3:
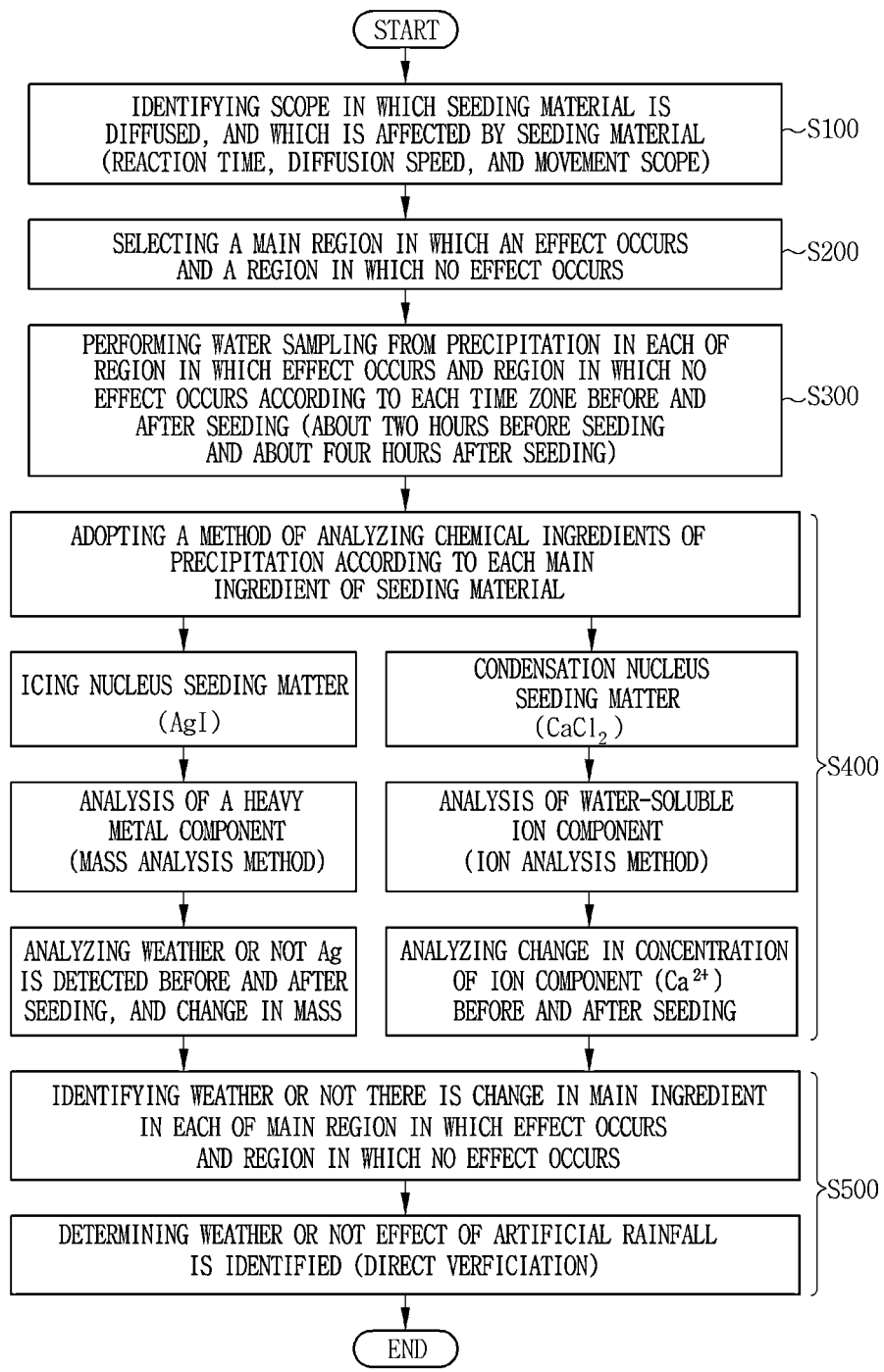
FIG. 3 is a detailed flow chart showing a method of analyzing ingredients of an artificial rainfall according to another embodiment of the present invention.

FIG. 1 is a flow chart showing a method of analyzing ingredients of an artificial rainfall according to one embodiment of the present invention, FIG. 2 is a detailed flow chart showing analyzing ingredients of water sampling matter shown in FIG. 1, and FIG. 3 is a detailed flow chart showing a method of analyzing ingredients of an artificial rainfall according to another embodiment of the present invention.

The concepts concerning the main region in which the effect occurs (i.e., a downwind region being affected by a diffusion reaction of the seeding material), and the region in which no effect occurs, observations on precipitation, and the analysis procedure of chemical ingredients, which are devised as a main method for direct verification of an artificial rainfall, are shown in FIG. 3.

In the present invention, the main region in which the effect occurs, that is, a region in which a seeding material is mainly diffused is defined as a first region, and the region in which no effect occurs, that is, a region in which no seeding material is diffused is defined as a second region.

First of all, in order to select an experimental scope of an experiment for an artificial rainfall, and a main region in which an effect occurs, weather information (i.e., satellite data, numerical model estimate data and so on) is collected. When an experimental altitude, a temperature condition, and so on are decided, the kind of a seeding material and a seeding amount are decided. When a kind of the seeding material, a seeding amount of the seeding material, a seeding altitude, a temperature condition, an initial direction of the wind, the condition of a wind speed, and so on are decided, a scope in which the seeding material is diffused, and which is affected by the seeding material is calculated by a numerical method as shown below.

In consideration of the calculated scope which is affected by the seeding material, when the main region in which the effect occurs (mainly a downwind area), and a region located in an upwind area in which no seeding material is diffused, and in which no effect occurs, are selected, a verification method is determined.

The verification method is divided into an indirect verification method using a numerical simulation, a change in radar reflectance, cloud physics-based observations, and so on, and a direct verification method using an experiment, water sampling from precipitation of each of comparative regions, and the analysis of ingredients.

In the present invention, since the direct verification method is described, the detailed description of the indirect verification method is omitted.

Referring to FIG. 1, a method of analyzing the ingredients of an artificial rainfall according to one embodiment of the present invention comprises (A) calculating a scope which is affected by seeding S100; (B) selecting a first region and a second region S200; (C) carrying out water sampling from precipitation before and after seeding S300; (D) analyzing ingredients of water sampling matter S400; and (E) verifying an effect of the artificial rainfall S500.

Here step (A) indicated by S100 shows calculating a scope in which a seeding material is diffused, and which is affected by seeding when a seeding condition for the artificial rainfall is decided as weather information is collected.

In step (A) indicated by S100, the weather information (satellite data, numerical model estimate data, and so on) is collected to select an experimental scope of the experiment for the artificial rainfall, and a main region in which an effect occurs. When an experimental altitude, a temperature condition, and so on are decided, the kind of a seeding material, and an amount of the seeding material are decided. When the kind of a seeding material, an amount of the seeding material, an altitude at which seeding is performed, a temperature, an initial direction of the wind, the condition of a wind speed, and so on are decided, a scope in which the seeding material is diffused, and which is affected by the seeding material is calculated by a numerical method.

A seeding material targeted for a warm cloud (having a temperature of 0° C. or more at a seeding altitude) is calcium chloride (CaCl2) which is condensation nucleus matter, and so on, and a seeding material targeted for a cool cloud (having a temperature of 0° C. or below at a seeding altitude) is silver iodide (AgI) which is icing nucleus matter, and so on.

Furthermore, step (B) indicated by S200 shows selecting a first region, namely, a main region which is largely affected by diffusion of the seeding material, and a second region, namely, a region which is slightly affected by diffusion of the seeding material in consideration of the scope which is affected by the seeding material.

In step (B) indicated by S200, in consideration of the calculated scope which is affected by the seeding material, when the main region (mainly a downwind area) in which an effect occurs, namely, the first region, and the region located in an upwind area in which no seeding material is diffused, and in which no effect occurs, namely, the second region are selected, the verification method is determined. The verification method is divided into an indirect verification method using a numerical imitation, a change in radar reflectance, cloud physics-based observations, and so on, and a direct verification method using an experiment, water sampling from precipitation of each of comparative regions, the analysis of ingredients, and so on, and in the present invention, the direct verification method is mainly described.

Furthermore, step (C) indicated by S300 shows performing water sampling from precipitation according to each time zone before and after seeding in the first region and the second region.

Here in step (C) indicated by S300, when the main region in which the effect occurs, and the region in which no effect occurs are identified, a precipitation-based water sampling instrument is installed at each of specific points of the selected regions so that water sampling from precipitation can be carried out according to each time zone before and after seeding. Time required for performing water sampling from precipitation may be set up as about 2 hours before seeding, and about 4 hours after seeding in consideration of the feature of each cloud targeted for seeding, or the feature of precipitation, time required for generating a reaction effect, and so on.

Furthermore, step (D) indicated by S400 shows analyzing ingredients of matter included in a water sample according to each temperature shown at a seeding altitude.

Here in step (D) indicated by S400, analysis of the ingredients is divided into the analysis of a water-soluble ion component, and the analysis of a heavy metal component according to each kind of the seeding material used.

Referring to FIG. 2, in step (D) indicated by S400, as the temperature of a cloud is measured at the seeding altitude S410, the seeding material according to the temperature of the cloud is analyzed.

First, in case that the cloud has the temperature of 0° C. or more, that is, a warm cloud is targeted, according to an experimental example, when an experiment for an artificial rainfall using calcium chloride (CaCl$_2$), which is condensation nucleus matter, is carried out, a concentration balance and a change level of an ion component before and after seeding are analyzed by analysis of the ion component S421. In particular, the priority analysis of a change in equivalent concentration of an nss-Ca$^{2+}$ ion (wherein nss represents non-sea salt) and a Cl$^-$ ion, which are main ingredients of the seeding material, is carried out, and analysis of each content of ingredients based on sea salt particles by an ion balance is excepted from the analysis of an effect resulting from the ingredients of the seeding material. The equivalent concentration is a concentration of the ion component included in each unit of a mole, and causes numerical values of the entire ions to be easily compared with each other. Meanwhile, in order to quantitatively calculate an increasing amount of nss-Ca$^{2+}$ which is a main ingredient of the artificial rainfall, it is required to consider a volume-weighted concentration which is calculated in such a manner that a volume-weighted value is provided on the basis of an annual amount of rainfall of the corresponding region. However, in the present invention, in case of the heavy metal component, since a change in ion concentration before and after seeding shown in the main region in which the effect occurs should first be considered, the detailed description concerning calculation of the volume-weighted concentration is omitted.

That is, in case that a cloud has a temperature of 0° C. or below at the seeding altitude, as a heavy metal component with respect to ingredients of icing nucleus matter included in a water sample is analyzed, whether or not a reference ingredient is detected before and after seeding, and a change in mass are analyzed, and in said step (E), the reference ingredient, which can cause the effect of the artificial rainfall to be verified, is the heavy metal component, wherein the reference ingredient becomes silver (Ag) in case that the icing nucleus matter is silver iodide.

Next, in case that a cloud has a temperature of 0° C. or below, namely, a cool cloud is targeted, according to an experimental example, when an experiment for the artificial rainfall using silver iodide (AgI), which is icing nucleus matter, is carried out, the main ingredient of the seeding material is analyzed by analysis of the heavy metal component S422. Whether or not the silver (Ag) component between the components, which is a main ingredient of the artificial rainfall, is detected, and a change according to each time resulting from a seeding effect are analyzed. Since the Ag component is a very stable metal element in a solid state, it is characteristic in that it is difficult to detect the component from natural precipitation by a chemical reaction, and thus although the Ag component exists, it exists in an infinitesimal quantity.

That is, in case that a cloud has a temperature of 0° C. or more at the seeding altitude, as a water-soluble ion component with respect to the ingredients of condensation nucleus matter included in a water sample is analyzed, whether or not a reference ingredient is detected before and after seeding, and a change in mass are analyzed, and in said step (E), a reference ingredient by which an effect of the artificial rainfall can be verified is the water-soluble ion component, and in case that the condensation nucleus matter is calcium chloride, the reference ingredient becomes a calcium divalent ion (Ca$^{2+}$) (referred to as "calcium ion" in the present invention).

Accordingly, when the mass concentration of Ca$^{2+}$ or Ag component, which is directly seeded in the cloud and detected, and a change according to each time zone before and after seeding are identified, it may finally be determined that an effect resulting from the experiment for the artificial rainfall exists in a main region which is estimated that an effect will occur S500. In order to identify a quantitative change level in the concentration of heavy metal, it is necessary to consider an annual background concentration like the volume-weighted concentration of the ion component as previously described. In the present invention, the description is omitted.

Furthermore, step (E) indicated by S500 shows verifying an effect of the artificial rainfall by determining a change in reference ingredient extracted in each of the first region and the second region.

Here step (E) indicated by S500 shows determining each change of the reference ingredients, namely, the heavy metal component extracted from the cool cloud in the first region and the water-soluble ion component extracted from the warm cloud in the second region, and determining that an experimental effect of the artificial rainfall exists in the first region when it is determined that there is a meaningful change in concentration of each of the reference ingredients before and after seeding.

In case that a cloud has a temperature of 0° C. at the seeding altitude, although all two experimental methods applied to the cases of the cool cloud and the warm cloud may be used, an experimenter can mainly determine a condition for these methods from his or her experience according to a meteorological status of the spot where the experiment is performed, and according to the present development, the experimental method is defined under the condition that the warm cloud is targeted.

Figure 4:
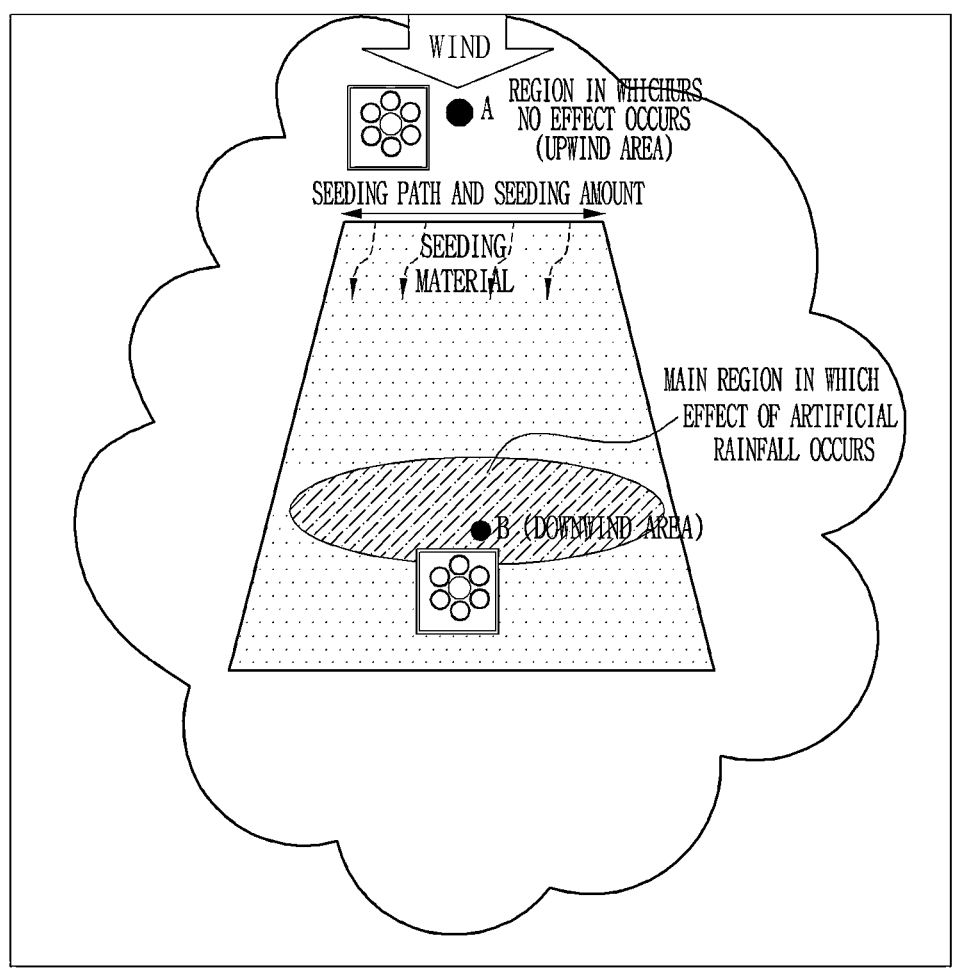
FIG. 4 is a horizontal concept view concerning each definition of a main region in which an effect occurs, and a region in which no effect occurs, and the arrangement of precipitation-based water sampling instruments according to an experiment for an artificial rainfall of the present invention.

FIG. 4, which is a horizontal concept view concerning the definitions of a main region in which an effect occurs and a region in which no effect occurs, and the arrangement of precipitation-based water sampling instruments according to an experiment for an artificial rainfall of the present invention, represents a horizontal concept view concerning the definitions of the main region in which the effect of the artificial rainfall occurs (ex., point B located at a downwind area), and the region in which no effect occurs (ex., point A located at an upwind area) according to a decision on a seeding path of the artificial rainfall, and the arrangement of the precipitation water sampling instruments for verification of ingredients of precipitation.

Referring to FIG. 4, a main region in which point B is included, and in which an effect of the artificial rainfall occurs corresponds to a first region which is mainly affected by diffusion of a seeding material, and a region in which point A is included, and in which no effect occurs corresponds to a second region in which a seeding material is hardly diffused. Also, this content is also applied to the cases shown in FIG. 5 to FIG. 7 without discrimination.

Selection of the main region in which the effect occurs (for example, a region indicated in the shadow, and point B) is aimed at a region in which the effect occurs as a rainfall (or a snowfall) by a dynamical and minute cloud-physical reaction process according to a kind of the seeding material of the artificial rainfall, a point at which seeding is carried out, a scope in which seeding is performed, a main direction of the wind, the condition of a wind speed, and so on. The region in which no effect occurs may be selected as an upwind point (point A) before an effect occurs due to a reaction of the seeding material, or a region in which a natural rainfall exists, it is difficult for the natural rainfall to generate an effect of activity of the seeding material, or so on. Here the natural rainfall region should be provided with a rainfall system which is cloud-physically identical to that of the artificial rainfall. A precipitation-based water sampling instrument is installed in each of the selected main region in which an effect occurs, and the selected region in which no effect occurs, and the analysis of chemical ingredients is carried out by performing water sampling from precipitation according to each time zone during about two hours before the experiment and about four hours after the experiment. About two hours before the experiment should be planed for observing a background concentration before an experiment effect of the artificial rainfall is found, and about four hours after the experiment should be planned for grasping a change in effect of the artificial rainfall.

Figure 5:
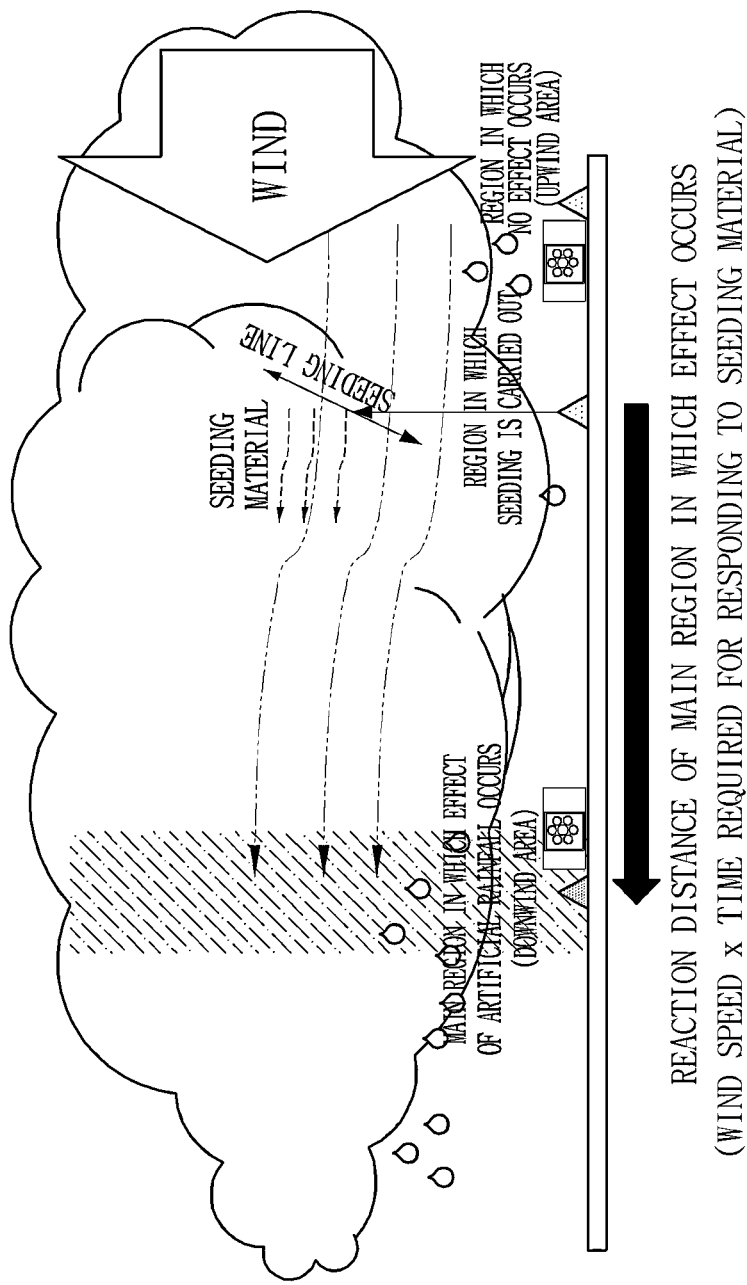
FIG. 5 is a vertically cross-sectional concept view concerning each definition of the region in which the main effect occurs and the region in which no effect occurs, and the arrangement of the precipitation-based water sampling instruments according to the experiment for the artificial rainfall of the present invention.

FIG. 5 is a vertically cross-sectional concept view concerning each definition of the main region in which the main effect occurs, and a region in which no effect occurs, and the arrangement of precipitation-based water sampling instruments according to the experiment for the artificial rainfall of the present invention.

FIG. 5 is a concept view in which the contents described on the basis of FIG. 4 are vertically constructed. First, a reaction distance of the main region in which the effect occurs is calculated by the time required for generating the effect of the seeding material, and a diffusion and movement speed of the system.

The reaction of the seeding material synthetically occurs according to an atmospheric temperature inside the cloud, a liquid water content in the cloud, a distribution according to each particle size of the seeding material and each size of cloud particles, the effect of an ascending current inside the cloud, and so on. In order to generate the main effect according to each ingredient of the seeding material, it takes about 20 minutes to 180 minutes (i.e., about one hour on an average) in case of silver iodide (AgI) which is icing nucleus matter, and it takes about 1 to 8 hours (i.e., about three hours on an average) in case of calcium chloride (CaCl2), which condensation nucleus matter. A reaction distance of the main region in which the effect occurs is mainly calculated by a numerical modeling technique, and based on a cloud physics-based information value calculated therefrom, the main region in which the effect occurs due to the seeding material of the artificial rainfall, and the region in which no effect occurs are selected. As the precipitation-based water sampling instrument is arranged at each of the points which is selected as the main region in which the effect occurs, and the region in which no effect occurs, comparative observations are carried out.

Reaction distance ($d$) of the main region in which the effect occurs (a wind speed×time required for responding to the seeding material)     [Mathematical Formula 1]

Reaction distance ($d$) of the main region in which the effect occurs (a wind speed×time required for responding to the seeding material)

Figure 6:
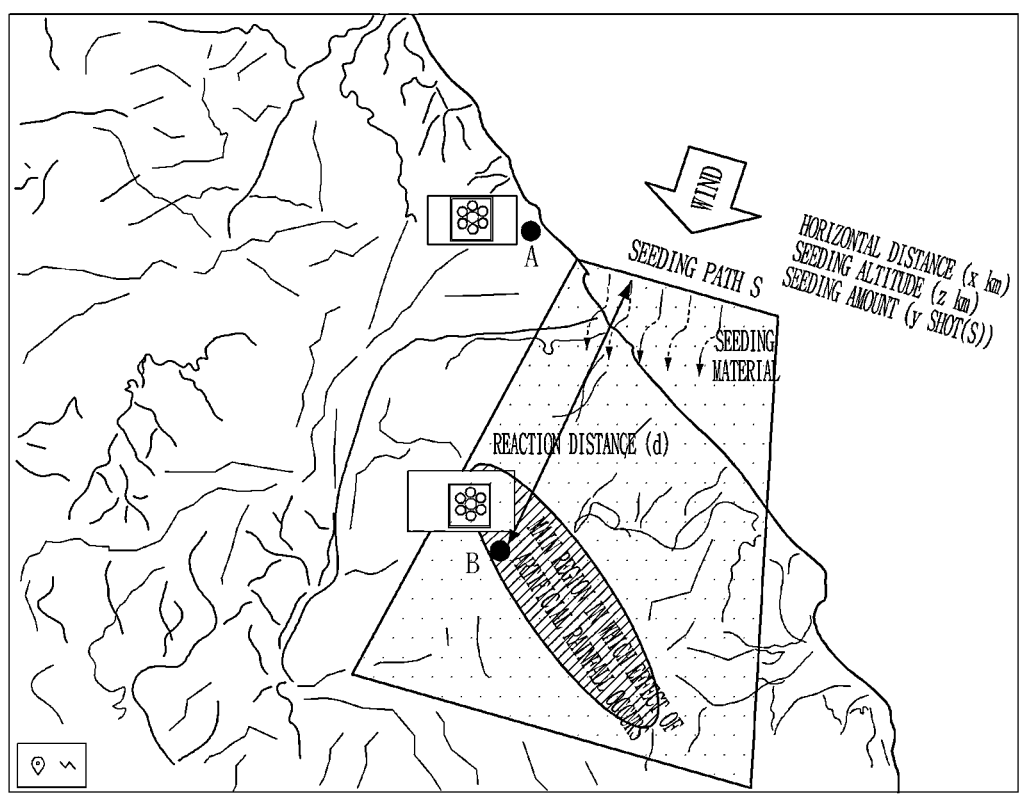
FIG. 6 is an exemplary view concerning a selection result of a main region in which an effect occurs, and a region in which no effect occurs, and points at which comparative observations on precipitation-based water sampling instruments are performed according to an experimental case for an artificial rainfall of the present invention.

FIG. 6 is an exemplary view concerning the selection result of a main region in which an effect occurs, and a region in which no effect occurs, and points at which comparative observations on the precipitation-based water sampling instruments are performed according to an experimental case for an artificial rainfall of the present invention.

Referring to FIG. 6, which is a horizontally cross-sectional example view concerning the selection result of the main region in which the effect occurs, and a region in which no effect occurs, and comparative points at which each of the precipitation-water sampling instruments is installed according to a case to which the present invention is practically applied, in the corresponding experiment case, burnt carbon (including CaCl2 as a main ingredient), which is condensation nucleus matter included in the seeding material, was used in an aerial experiment targeted for a warm cloud, and with regard to a burnt amount, y shot(s) in seeding amount was (were) used according to a seeding path S (a horizontal distance×km), and a seeding altitude z km. The main region in which the effect of the seeding material occurs, and the region in which no effect occurs were selected by a numerical modeling result, and the precipitation-based water sampling instrument was installed and operated at each point, point B selected as the main region in which the effect occurs, and point A selected as the region in which no effect occurs within a scope of the selected areas. A horizontal reaction distance d between point B selected as the main region in which the effect occurs and a point at which seeding is performed was estimated at about d (=v×t) km on the basis of expected time t required for generating the largest effect (i.e., about 1 hour to 3 hours in case of condensation nucleus matter), an average wind speed v and so on.

$$\text{Horizontal reaction distance } (d) \text{ between points at which seeding is performed} = v \times t \quad \text{[Mathematical Formula 2]}$$

Figure 7:
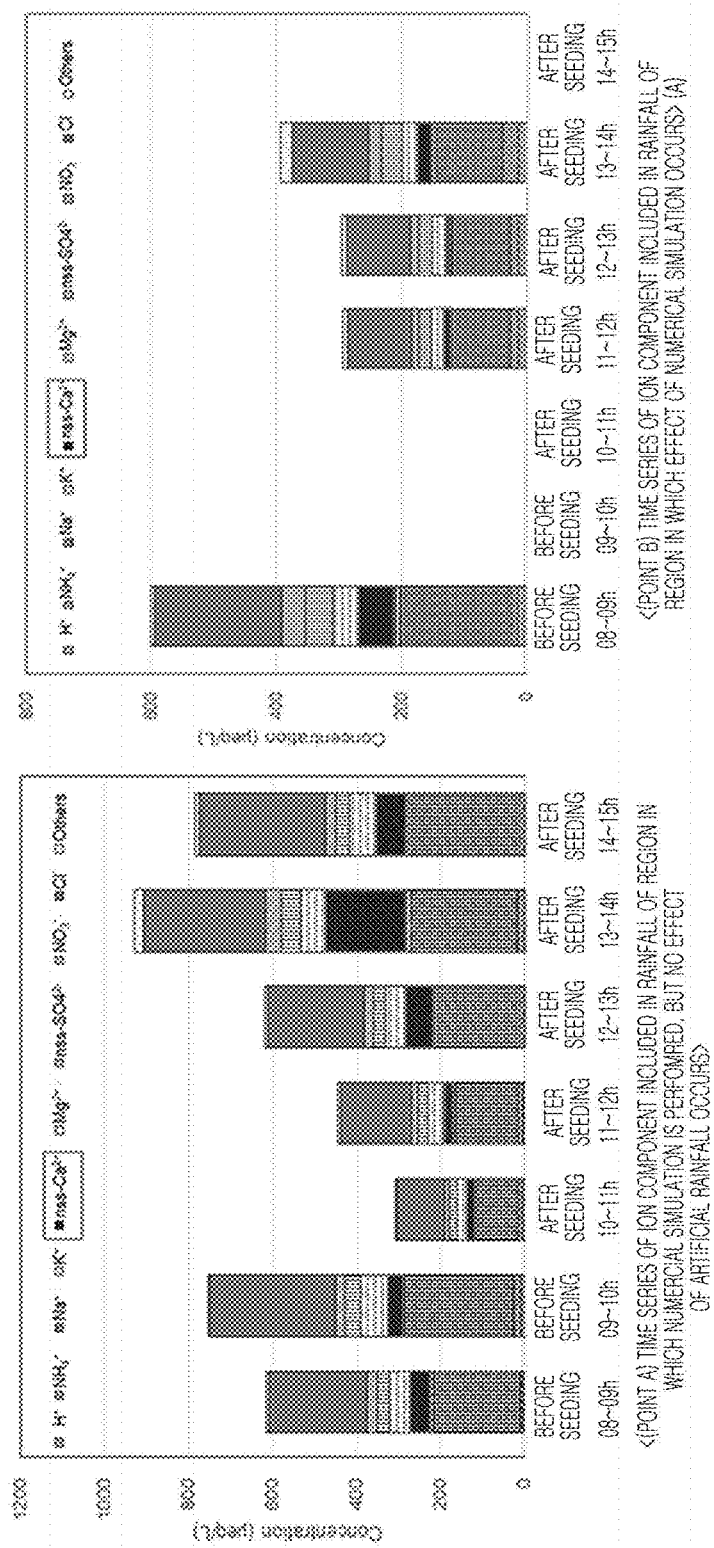
FIG. 7 is an exemplary view concerning a result of analyzing chemical ingredients of precipitation from each of the main region in which the effect occurs and the region in which no effect occurs according to the case to which the present invention is actually applied.

FIG. 7 is an exemplary view concerning the analysis results of chemical ingredients of precipitation shown in the main region in which the effect occurs, and the region in which no effect occurs according to the case to which the present invention is actually applied.

Referring to FIG. 7, which is an exemplary view showing the analysis results of the ingredients of precipitation shown from a main point at which the effect occurs, and a point at which no effect occurs according to the case to which the present invention is practically applied, since this case applied represents a case in which hygroscopic burnt carbon (calcium chloride $CaCl_2$), which is an icing nucleus seeding material, is used under the condition that a warm cloud is targeted, a change in concentration of a calcium ion from which the effect of sea salt is removed (nss-$Ca^{2+}$) acts as an important fluent. Although time series concerning the ion component of precipitation of point B selected as a main point at which an effect occurs shows that there is hardly a change in each equivalent concentration of the ingredients of the artificial rainfall (nss-$Ca^{2+}$) before and after seeding, while the rainfall slowly increases after seeding, the largest effect of the increase in the rainfall is generated after about 3 hours to 4 hours, and then showing a tendency to gradually decrease. Time required for generating the largest effect of the increasing rainfall may be analyzed to be similar to the time required for generating the reaction effect of the artificial rainfall (1 hour to 3 hours) in case of the hygroscopic seeding material as previously described. In case of point A selected as the region in which no effect occurs, although a numerical simulation is performed, a change level in each concentration of chemical ingredients of the artificial rainfall before and after seeding is hardly found in the region in which no effect of the artificial rainfall occurs. The above-mentioned result is a result value concerning a single example, and is determined as an exemplary datum that is good to explain the present concept.

(A) of FIG. 7 represents time series of the ion component in case of the region located at point B in which the effect occurs due to the numerical simulation, and (B) of FIG. 7 represents time series of the ion component in case of the region located at point B in which the numerical simulation is performed, but no effect of the artificial rainfall occurs.

Next, a system of analyzing ingredients of an artificial rainfall according to the other embodiment of the present invention is described.

Figure 8:
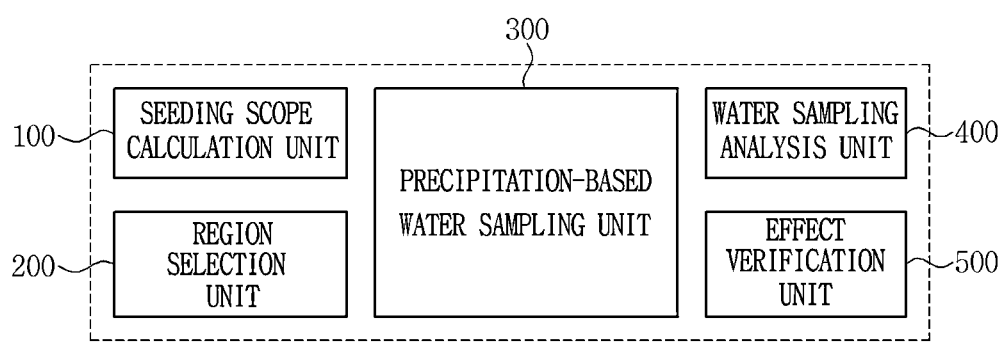
FIG. 8 is a block diagram showing a system of analyzing ingredients of an artificial rainfall according to the other embodiment of the present invention.

FIG. 8 is a block diagram showing the system of analyzing ingredients of an artificial rainfall.

Referring to FIG. 8, the artificial rainfall ingredient analysis system comprises: a seeding scope calculation unit 100; a region selection unit 200; a precipitation-based water sampling unit 300; a water sampling analysis unit 400; and an effect verification unit 500.

Here the seeding scope calculation unit 100 calculates a scope in which a seeding material is diffused, and which is affected by the seeding material when a seeding condition for the artificial rainfall is decided as weather information is collected.

In order to select an experimental scope applied to the experiment for the artificial rainfall, and a main region in which an effect occurs, weather information (i.e., satellite data, numerical model estimate data, etc.) is collected. When an experimental altitude, a temperature condition, and so on are decided, a kind of the seeding material, and a seeding amount are decided. When a kind of the seeding material, a seeding amount, an altitude at which seeding is performed, a temperature, an initial direction of the wind, the condition of a wind speed, and so on are decided, a scope in which the seeding material is diffused, and which is affected by the seeding material is calculated by a numerical method.

The seeding material targeted for a warm cloud (having a temperature of 0° C. or more at a seeding altitude) is calcium chloride (CaCl2) which is condensation nucleus matter, and so on, and the seeding material targeted for a cool cloud (having a temperature of 0° C. or below at a seeding altitude) is silver iodide (AgI), which icing nucleus matter, and so on.

Furthermore, the region selection unit 200 selects a first region, a main region which is largely affected by diffusion of the seeding material, and a second region which is slightly affected by the diffusion of the seeding material in consideration of the scope which is affected by the seeding material.

When the region selection unit 200 selects a main region in which an effect occurs (mainly, a downwind area), namely, the first region, and a region located in an upwind area in which neither seeding material is diffused, nor effect occurs, namely, the second region, a verification method is determined. The verification method is divided into an indirect verification method using a numerical simulation, a change in radar reflectance, cloud physics-based observations, and so on, and a direction verification method using an experiment, water sampling from precipitation of each of comparative regions, the analysis of ingredients, and so on, and in the present invention, the direct verification method is mainly described.

Also, the precipitation-based water sampling unit 300 performs water sampling from precipitation according to each time zone before and after seeding in the first region and the second region.

Here when the main region in which the effect occurs, and the region in which no effect occurs are identified, a precipitation-based water sampling instrument is installed at each specific point of the selected regions, and thus the precipitation-based water sampling unit 300 performs water sampling from precipitation according to each time zone before and after seeding. Time required for performing the water sampling from precipitation may be set up as about 2 hours before seeding and about 4 hours after seeding in consideration of the feature of a cloud targeted for seeding, or the feature of precipitation, time required for generating a reaction effect, and so on.

Furthermore, the water sampling analysis unit 400 analyzes ingredients of matter included in a water sample according to each temperature shown at the seeding altitude.

Here analysis of the ingredients carried out by the water sampling analysis unit 400 is divided into the analysis of a water-soluble ion component and the analysis of a heavy metal component according to the kind of the seeding material used.

Referring to FIG. 2, the water sampling analysis unit 400 measures the temperature of a cloud at the seeding altitude, thereby analyzing the seeding material according to each temperature of the cloud.

First, in case that the cloud is a temperature of 0° C. or more, namely, a warm cloud is targeted, according to an experimental example, when an experiment for an artificial rainfall using calcium chloride (CaCl2), which is condensation nucleus matter, is carried out, the concentration balance and change level of an ion component before and after seeding are analyzed by analysis of the ion component. In particular, the priority analysis of a change in equivalent concentration of an nss-$Ca^{2+}$ ion (wherein nss represents non-sea salt) and a $Cl^-$ ion, which are main ingredients of the seeding material, is carried out, and the analysis of each content of ingredients on the basis of sea salt particles by an ion balance is excepted from the analysis of an effect resulting from the ingredients of the seeding material. The equivalent concentration is a concentration of the ion component included in each unit of a mole, and causes numerical values of the entire ions to be easily compared with each other. On the other hand, in order to quantitatively calculate an increasing amount of nss-$Ca^{2+}$ which is a main ingredient of the artificial rainfall, it is necessary to consider a volume-weighted concentration, which is calculated in such a manner that a volume-weighted value is provided based on an annual amount of rainfall of the corresponding region. However, in the present invention, in case of the heavy metal component, since a change in ion concentration before and after seeding shown in the main region in which the effect occurs, and the region in which no effect occurs should first be considered, the detailed description concerning calculation of the volume-weighted concentration is omitted.

That is, in case that a cloud has a temperature of 0° C. or below at the seeding altitude, whether or not a reference ingredient before and after seeding is detected, and a change in mass are analyzed by analysis of a heavy metal component with respect to ingredients of icing nucleus matter included in a water sample, and a reference ingredient, which can cause an effect of the artificial rainfall to be verified by the effect verification unit 500, is the heavy metal component, wherein in case that the icing nucleus matter is silver chloride (AgI), the reference ingredient becomes silver (Ag).

Next, in case that a cloud has a temperature of 0° C. or below, namely, a cool cloud is targeted, according to an experimental example, when an experiment for the artificial rainfall using silver iodide (AgI), which is icing nucleus matter, is performed, a main ingredient of the seeding material is analyzed by the analysis of a heavy metal component. Whether or not Ag (silver) component between the components, which is a main ingredient of the artificial rainfall, is detected, and a change according to each time resulting from a seeding effect are analyzed. Since the Ag component is a very stable metal element in a solid state, it is characteristic in that it is difficult to detect the component through a chemical reaction in natural precipitation, although the Ag component exists, it exists in an infinitesimal quantity.

That is, in case that a cloud has a temperature of 0° C. or more at the seeding altitude, as a water-soluble ion component with respect to ingredients of condensation nucleus matter is analyzed, whether or not a reference ingredient is detected before and after seeding, and a change in mass are analyzed, wherein the reference ingredient, which can cause the effect of the artificial rainfall to be verified by the effect verification unit 500, is the water-soluble ion component, and in case that condensation nucleus matter is calcium chloride, the reference ingredient becomes a calcium ion ($Ca^{2+}$).

Accordingly, when the mass concentration of Ag component which is directly seeded into the cloud and detected, a change according to each time zone before and after seeding are identified, the effect verification unit 500 may finally determine that an effect resulting from the experiment for the artificial rainfall occurs in the main region in which the effect is estimated to occur. In order to identify a quantitative change level in concentration of heavy metal, although it is necessary to consider an annual background concentration, such as the volume-weighted concentration of the ion component as previously described, in the present invention, the description is omitted.

Furthermore, the effect verification unit 500 verifies the effect of the artificial rainfall by determining a change in the reference ingredient extracted in each of the first region and the second region.

Here the effect verification unit 500 determines each change in the reference ingredients extracted in the first region and the second region, namely, each change in the heavy metal component extracted from the cool cloud and the water-soluble ion component extracted from the warm cloud, and also determines that an effect resulting from the experiment for the artificial rainfall occurs in the first region when it is determined that there is a meaningful change in concentration of each of the reference ingredients.

In case that a cloud has a temperature of 0° C. at a seeding altitude, although all two experimental methods applied to the cases of the cool cloud and the warm cloud can be used, an experimenter can mainly determine a condition for these methods from his or her experience according to a meteorological status of the spot where the experiment is performed, and according to the present development, the experimental method is defined under the condition that the warm cloud is targeted.

As described above, although it is mentioned that all the constituent elements, which constitute the embodiments of the present invention, are combined with each other as one element, or are operated in a state of being combined, the present invention should not be limited to these embodiments. That is, all the constituent elements may be operated in such a manner that one or more constituent elements are selectively combined with each other, if this combination falls within the scope of the objects of the present invention. Also, each of all the constituent elements may be embodied in one dependent hardware form, and may also be embodied in a computer program form having a program module intended for performing part or all parts of the function, which is prepared in a plurality of hardware. Codes and code segments, which constitute the computer program, can easily be induced by those having ordinary skill in the technical field to which the present invention pertains. This computer program is read and operated by a computer in a state of being saved in a computer-readable medium so that the embodiments of the present invention can be implemented.

What is claimed is:

1. A method for performing an artificial rainfall, comprising:
- receiving weather information from a satellite, the weather information including, at least, temperature of clouds, a direction of the wind, and a speed of the wind;
- selecting, by a central processing unit (CPU) of an operational system, a seeding material for seeding based on the weather information, wherein:
  - when the temperature of clouds is 0° C. or below at the seeding altitude, the CPU selects an icing nucleus matter as the seeding material, and the icing nucleus matter is seeded, and
  - when the temperature of clouds is more than 0° C. at the seeding altitude, the CPU selects a condensation nucleus matter as the seeding material and the condensation nucleus matter is seeded;
- calculating, by the CPU, a scope in which the seeding material is diffused using the weather information, a kind of the seeding material, an amount of the seeding material, and a seeding altitude;
- selecting, by the CPU, a first region and a second region by considering the direction of the wind and the speed of the wind, wherein the first region is an area expected to be affected by diffusion of the seeding material, and the second region is an area expected not to be affected by diffusion of the seeding material;
- taking water samples from precipitation by water sampling instruments installed at specific points in the first region and the second region, the water samples being taken at regular time intervals before and after seeding, respectively;
- extracting, by a water sample analyzer, reference ingredients included in the water samples, wherein the reference ingredients are selected based on the temperature of clouds such that when the temperature of clouds is 0° C. or below at the seeding altitude, an existence of a heavy metal component included in the icing nucleus matter and a change in mass of the heavy metal component before and after seeding are selected as the reference ingredients, and when the temperature of clouds is more than 0° C. at the seeding altitude, an existence of a water-soluble ion component included in a condensation nucleus matter and a change in mass of the water-soluble ion component before and after seeding are selected as the reference ingredients; and
- verifying, by the CPU, an effect of the artificial rainfall based on the existence and the change in mass of the reference ingredients extracted from the water samples in each of the first region and the second region, and adjusting the kind of seeding material, the amount of the seeding material and the seeding altitude for next performance of the artificial rainfall based on verifying the effect of the artificial rainfall.

2. The method of claim 1, wherein the icing nucleus matter is silver iodide, the CPU verifies the effect based on an existence of a silver included in the icing nucleus matter and a change in mass of the silver before and after seeding.

3. The method of claim 1, wherein the condensation nucleus matter is calcium chloride, the CPU verifies the effect based on an existence of a calcium ion included in the condensation nucleus matter and a change in mass of the calcium ion before and after seeding.

4. A system for performing an artificial rainfall, comprising:
- a satellite configured to obtain weather information including, at least, temperature of clouds, a direction of the wind, and a speed of the wind;
- a central processing unit (CPU) configured to:
  - select a seeding material for seeding based on the weather information, wherein:
    - when the temperature of clouds is 0° C. or below at the seeding altitude, the CPU selects an icing nucleus matter as the seeding material to be seeded, and
    - when the temperature of clouds is more than 0° C. at the seeding altitude, the CPU selects a condensation nucleus matter as the seeding material to be seeded, and
  - calculate a scope in which the seeding material is diffused using the weather information received from the satellite, a kind of seeding material, an amount of the seeding material and a seeding altitude, wherein the CPU selects a first region and a second region by considering the direction of the wind and the speed of the wind, the first region being an area expected to be affected by diffusion of the seeding material, and the second region being an area expected not to be affected by diffusion of the seeding material;
- water sampling instruments configured to take water samples from precipitation at regular interval, the water sampling instruments being installed at specific points in the first region and the second region; and
- a water sample analyzer configured to extract reference ingredients included in the water samples, wherein the reference ingredients are selected based on the temperature of clouds such that when the temperature of clouds is 0° C. or below at the seeding altitude, an existence of a heavy metal component included in the icing nucleus matter and a change in mass of the heavy metal component before and after seeding are selected as the reference ingredients, and when the temperature of clouds is more than 0° C. at the seeding altitude, an existence of a water-soluble ion component included in the condensation nucleus matter and a change in mass of the water-soluble ion component before and after seeding are the reference ingredients,
- wherein the CPU is configured to verify an effect of the artificial rainfall based on the existence and the change in mass of the reference ingredients extracted from the water samples in each of the first region and the second region, and to adjust the kind of seeding material, the amount of the seeding material and the seeding altitude for next performance of the artificial rainfall based on verifying the effect of the artificial rainfall.

5. The system of claim 4, wherein the icing nucleus matter is silver iodide, the CPU verifies the effect based on reference ingredients an existence of a silver included in the icing nucleus matter and a change in mass of the silver before and after seeding.

6. The system of claim 4, wherein the condensation nucleus matter is calcium chloride, the CPU verifies the effect based on an existence of a calcium ion included in the condensation nucleus matter and a change in mass of the calcium ion before and after seeding.

* * * * *